United States Patent
Stone et al.

(10) Patent No.: US 10,665,134 B2
(45) Date of Patent: May 26, 2020

(54) SURGICAL TRAINING APPARATUS, METHODS AND SYSTEMS

(71) Applicant: Simulated Inanimate Models, LLC, Pittsford, NY (US)

(72) Inventors: Jonathan Stone, Rochester, NY (US); Steven Griffith, Honeoye Falls, NY (US); Nelson N. Stone, Vail, CO (US)

(73) Assignee: Simulated Inanimate Models, LLC, Pittsford, NY (US)

( * ) Notice: Subject to any disclaimer, the term of this patent is extended or adjusted under 35 U.S.C. 154(b) by 0 days.

(21) Appl. No.: 16/525,029

(22) Filed: Jul. 29, 2019

(65) Prior Publication Data
US 2020/0027374 A1 Jan. 23, 2020

Related U.S. Application Data

(62) Division of application No. 16/039,025, filed on Jul. 18, 2018, now Pat. No. 10,410,542.

(51) Int. Cl.
| | |
|---|---|
| G09B 23/30 | (2006.01) |
| G09B 23/28 | (2006.01) |
| A61B 34/30 | (2016.01) |
| G06F 3/01 | (2006.01) |
| G06T 19/00 | (2011.01) |

(52) U.S. Cl.
CPC ......... *G09B 23/30* (2013.01); *G09B 23/285* (2013.01); *A61B 34/30* (2016.02); *G06F 3/011* (2013.01); *G06T 19/006* (2013.01)

(58) Field of Classification Search
CPC .......... G09B 23/30; G09B 9/00; A61B 34/76; A61B 2017/00115; A61B 2017/00716; A61B 34/10; G06F 19/00
See application file for complete search history.

(56) References Cited

U.S. PATENT DOCUMENTS

| | | |
|---|---|---|
| 5,445,166 A | 8/1995 | Taylor |
| 6,336,812 B1 | 1/2002 | Cooper et al. |
| 6,474,993 B1 | 11/2002 | Grund et al. |
| 6,596,402 B2 | 7/2003 | Soerens et al. |
| 6,685,481 B2 | 2/2004 | Chamberlain |
| 6,780,016 B1 | 8/2004 | Toly |

(Continued)

FOREIGN PATENT DOCUMENTS

| | | |
|---|---|---|
| CN | 202003575 | 10/2011 |
| DE | 102013214402 | 9/2014 |

(Continued)

OTHER PUBLICATIONS

Gawande et al. "An Apgar Score for Surgery" American College of Surgeons, 2007, pp. 201-209.

(Continued)

*Primary Examiner* — Jerry-Daryl Fletcher
(74) *Attorney, Agent, or Firm* — Woods Oviatt Gilman LLP; Katherine H. McGuire, Esq.

(57) ABSTRACT

Surgical training apparatus, methods and systems which allow surgical trainees to practice surgical skills on anatomical models in a realistic manner with an augmented reality headset and delivery of targeted surgical coursework curriculum correlated to the actions of the trainee as sensed by sensors in or adjacent the model to help the trainee develop proper surgical technique and decision making.

12 Claims, 11 Drawing Sheets

(56) References Cited

U.S. PATENT DOCUMENTS

| | | |
|---|---|---|
| 6,857,878 B1 | 2/2005 | Chosack et al. |
| 6,863,536 B1 | 3/2005 | Fisher et al. |
| 7,083,418 B2 | 8/2006 | Baldauf |
| 7,665,995 B2 | 2/2010 | Toly |
| 7,850,456 B2 | 12/2010 | Chosack et al. |
| 8,029,824 B2 | 10/2011 | Osada et al. |
| 8,403,676 B2 | 3/2013 | Frassica et al. |
| 8,465,771 B2 | 6/2013 | Wan et al. |
| 8,708,707 B2 | 4/2014 | Hendrickson et al. |
| 8,801,438 B2 | 8/2014 | Sakezles |
| 8,834,170 B2 | 9/2014 | Kurenov et al. |
| 8,870,576 B2 | 10/2014 | Millon et al. |
| 8,961,190 B2 | 2/2015 | Hart et al. |
| 8,968,003 B2 | 3/2015 | Hendrickson et al. |
| 8,992,230 B2 | 3/2015 | Tuchschmid et al. |
| 9,096,744 B2 | 8/2015 | Wan et al. |
| 9,186,436 B2 | 11/2015 | Wan et al. |
| 9,218,753 B2 | 12/2015 | Hoke et al. |
| 9,328,327 B2 | 5/2016 | Haverich |
| 9,449,532 B2 | 9/2016 | Black et al. |
| 10,081,727 B2 | 9/2018 | Felsinger et al. |
| 10,083,631 B2 | 9/2018 | Forte et al. |
| 10,083,632 B2 | 9/2018 | Ristolainen et al. |
| 10,140,889 B2 | 11/2018 | Black et al. |
| 10,319,259 B2 | 6/2019 | Kerins et al. |
| 10,354,556 B2 | 7/2019 | Hofstetter |
| 10,410,542 B1 | 9/2019 | Stone et al. |
| 2004/0062809 A1 | 4/2004 | Honiger et al. |
| 2005/0100873 A1 | 5/2005 | Meythaler et al. |
| 2006/0209019 A1* | 9/2006 | Hu .................... G06F 3/016 345/156 |
| 2008/0070225 A1 | 3/2008 | Vezina et al. |
| 2009/0246747 A1 | 10/2009 | Buckman, Jr. |
| 2010/0047752 A1 | 2/2010 | Chan et al. |
| 2010/0311025 A1 | 12/2010 | Everett |
| 2012/0045743 A1 | 2/2012 | Okano et al. |
| 2012/0189998 A1 | 7/2012 | Kruecker et al. |
| 2013/0288218 A1 | 10/2013 | Mallin et al. |
| 2014/0011172 A1* | 1/2014 | Lowe .................... G09B 23/30 434/273 |
| 2014/0081652 A1* | 3/2014 | Klindworth ............ G06Q 10/10 705/2 |
| 2014/0106329 A1 | 4/2014 | Watanabe et al. |
| 2014/0322688 A1 | 10/2014 | Park et al. |
| 2015/0132732 A1 | 5/2015 | Hart et al. |
| 2016/0071437 A1 | 3/2016 | Hoke et al. |
| 2016/0284238 A1 | 9/2016 | Sekino et al. |
| 2016/0284242 A1 | 9/2016 | Sekino et al. |
| 2016/0284243 A1 | 9/2016 | Sekino et al. |
| 2016/0372010 A1 | 12/2016 | Hokazono |
| 2017/0032699 A1 | 2/2017 | Sekino et al. |
| 2017/0032700 A1 | 2/2017 | Seto et al. |
| 2017/0032701 A1 | 2/2017 | Sekino et al. |
| 2017/0032703 A1 | 2/2017 | Sekino et al. |
| 2017/0032704 A1 | 2/2017 | Sekino et al. |
| 2017/0032705 A1 | 2/2017 | Sekino et al. |
| 2017/0032706 A1 | 2/2017 | Sekino et al. |
| 2017/0136692 A1 | 5/2017 | Zheng et al. |
| 2017/0239886 A1 | 8/2017 | Norikane |
| 2017/0249872 A1 | 8/2017 | Piron et al. |
| 2017/0270831 A1 | 9/2017 | Norikane et al. |
| 2017/0278429 A1 | 9/2017 | Slanda et al. |
| 2017/0301264 A1 | 10/2017 | Vara et al. |
| 2017/0307598 A1 | 10/2017 | Skardal et al. |
| 2017/0333007 A1 | 11/2017 | Kim et al. |
| 2017/0360551 A1 | 12/2017 | Liu |
| 2018/0033339 A1 | 2/2018 | Kerins et al. |
| 2018/0035962 A1 | 2/2018 | Benndorf et al. |
| 2018/0047303 A1 | 2/2018 | Groenewald |
| 2018/0049622 A1 | 2/2018 | Ryan et al. |
| 2018/0049838 A1 | 2/2018 | Mitani et al. |
| 2018/0053441 A1 | 2/2018 | Slanda et al. |

FOREIGN PATENT DOCUMENTS

| | | |
|---|---|---|
| EP | 2996105 | 3/2016 |
| WO | 2015027286 | 5/2015 |

OTHER PUBLICATIONS

"Synthetic Tissue Phantoms" Cambridge Polymer Group, http://www.campoly.com/cpg-services/biomedical-materials/synthetic-tissue-phantoms/ (Accessed Jul. 10, 2017).

Ventola "Medical Applications for 3D Printing: Current and Projected Uses" P&T, 2014, vol. 39, pp. 704-712.

Carbone, Marina, et al. "Surgical simulators integrating virtual and physical anatomies." EICS4Med 2011 4.6 (2011).

Akhtar, K. S. N., et al. "The role of simulation in developing surgical skills." Current reviews in musculoskeletal medicine 7.2 (2014): 155-160.

Muns, Andrea, Jürgen Meixensberger, and Dirk Lindner. "Evaluation of a novel phantom-based neurosurgical training system." Surgical neurology international 5 (2014).

Surry KJ,et al. Poly (vinyl alcohol) cryogel phantoms for use in ultrasound and MR imaging. Phys Med Biol. Dec. 21, 2004;49(24):5529-46. Imaging Research Laboratories, Robarts Research Institute, London, Canada.

* cited by examiner

SURGICAL TRAINING APPARATUS, METHODS AND SYSTEMS

BACKGROUND OF THE INVENTION

The present invention relates to apparatus, methods and systems for surgical training. More particularly, the present invention relates to novel simulated surgical training apparatus, methods and systems which employ anatomy models with strategically placed sensors. The sensor equipped models are used in conjunction with an augmented reality headset and computer software to deliver guided instruction and targeted curricular content to the trainee at ideal times during a simulated surgical training session.

Many surgical trainees currently practice on live patients in the operating room due to insufficient alternatives. This may lead to less than ideal patient outcomes and unnecessarily increased operation times. Studies have shown that longer operating times add to patient risk and increase the cost of care.

Training on surgical phantom models is known, however, there still remains a need for improved surgical training apparatus, methods and systems. Specifically, surgical training requires both visual and verbal cues whilst the student is completing a motor task. Currently, the only means to provide this instruction is through live experienced practitioner training session. Unfortunately due to surgeon time constraints, in person training is only feasible during actual patient cases and therefore has the potential of causing harm or creating excessive costs due to surgical inefficiency.

SUMMARY OF THE INVENTION

Surgical training apparatus, methods and systems which allow surgical trainees to practice surgical skills on anatomical models in a realistic manner with an augmented reality headset and delivery of targeted surgical coursework curriculum correlated to the actions of the trainee as sensed by sensors in or adjacent the model to help the trainee develop proper surgical technique and decision making.

The present invention further addresses the above need by providing in another aspect sensor equipped surgical phantom models with integrated digital curricular content through an augmented reality headset (AR) or other human computer interface (HCl).

The present invention provides in yet another aspect information transfer between surgical phantoms, surgical tools, and computer software that allow a user to perform self-guided training.

In yet a further aspect, the present invention provides a surgical training phantom that emits signals in order to prompt delivery of curriculum content.

Signals can be generated from models using any suitable electronic components such as, for example, transducers, video images and/or strain gauges.

The generation of signals may be initiated in any one of or combination of ways, such as, for example:
a) upon sensing a change in the model such as, for example, the marking of a proposed incision site, the making of an incision, the onset of simulated bleeding, the resection of a simulated tumor, etc.;
b) upon sensing user movement such as user hand and/or head motions, for example;
c) sensing the use of a surgical instrument such as body marking pens, suture needles, needle drivers, laparoscopic instruments, suction tips, etc.; and/or
d) sensing a particular video field of view ("FOV") within the surgical field or "what the surgeon sees" during the course of the procedure.

Signals from sensors (e.g., transducers, electromagnetic spectrum emissions including visible and non-visible frequencies) are delivered to a computer running a surgical training software program using any desired communication mode such as camera vision, Wi-Fi, Bluetooth, sound, light, wired connection, etc. Machine learning may be employed to parse data, learn from that data and make informed decisions on what it has learned. Deep learning is a type of machine learning in which a model learns to perform classification tasks directly from images, texts, or signals. Deep learning may be implemented using neural network architecture which may be computed in real-time by parallel computers. Machine learning and/or Deep learning may be used to identify, process and classify objects using the signals and images from the AR headset camera and 9 degree of freedom head/camera position tracker and other signal outputs from the simulated organs and/or surgical instruments.

Signals are interpreted by the computer surgical training software program and may cause a state change in the surgical simulation training software.

The software may be programmed to deliver tutorial and "how-to" guides to the trainee that correspond to ongoing progress of the surgical phantom model training session.

In yet another aspect, the invention provides an AR platform that detects a surgical trainee's specific performance during a training procedure on a surgical model and responds to the detected performance by delivering to the trainee corresponding curricular content and/or other information. The AR headset and/or any video or camera feed including, e.g., video from a surgical instrument (laparoscope, endoscope, arthroscope, microscope, etc.), is able to detect one or more "Cues" which may be "Model Cues" and/or "Motion Cues" and/or "Still Image/Video Cues".

"Model Cues" are discrete elements or physical conditions emanating from the model itself which are detectable by a "Cue Receiver" such as the AR headset. Examples of Model Cues include, but are not limited to, physical markings (e.g., bar codes or other symbols in visible or nonvisible inks), electronic and/or optical sensors and/or any other fiducials embedded within or applied to the outer surface of the surgical model.

"Identification (ID) and/or Motion Cues" (hereinafter "ID-Motion Cues") include detection of physical presence (static state) and/or motions by the trainee (e.g., eye, head, hand, arm movements) and/or a surgical instrument which are detectable by the AR headset. In this regard, the trainee's body parts and/or the surgical instruments (including auxiliary items which may be used in the surgery such as clips, sponges and gauze, for example) may be provided with applied (e.g., temporary stick-on) sensors and/or other fiducials that allow detection of the presence (ID) and/or motion thereof. The motion detection may or may not be made trackable through a computerized navigation system.

"Still Image/Video Cues" include image capture and video feeds from surgical cameras (e.g., laparoscopic, robotic, etc.). The AR headset may also have image capture and video feed functionality which creates the input to the surgical system training software program.

Detection of Model Cues and/or ID-Motion Cues and/or Still Image/Video Cues by the Cue Receiver generates a signal which the surgical training system software (to which the Cue Receiver is wired or wirelessly connected) is programmed to interpret as a specific action and/or anatomical reference point of the model within the context of the particular surgical training module or session.

The Model Cues are strategically positioned in or on the model in a manner which corresponds with the software programming for that particular model. More particularly, the software may be programmed for a particular surgical training module. The software may thus be programmed with an ordered (and, optionally, timed) sequence of surgical acts on the model which are indicative of a successful surgical procedure for that particular surgical training module. The types and placement of the one or more Model Cues in or on the model and/or the ID-Motion Cues and/or the Still Image/Video Cues are correlated to the programmed ordered sequence of surgical acts for the particular surgical session. Should the trainee perform surgical acts on the model that are not in agreement with the expected surgical performance as identified in the software program, the software will detect any such digressions and respond by informing the trainee of the digression from the expected surgical protocol.

Curriculum content and/or other information may be automatically generated and delivered to the trainee at the time of the detected digression and/or at the conclusion of the training module.

Besides being able to detect a change in the programmed ordered sequence and/or timing of Model Cue detections, the Model Cues and/or Motion Cues and/or Image Capture/Video Cues may provide signals to the software indicative of a surgical act being performed on the model that is not according to protocol for that training module or not meeting the surgical performance standard for that act (e.g., marking the wrong site for an incision on the model with the body marking pen, poorly executing an incision, resection, or improper placement of a surgical instrument or auxiliary item (such as leaving a sponge in the model).

The system may thus detect the current surgical training state based on a detected Model Cue and/or ID-Motion Cue and/or Image Capture/Video Cues and respond by causing the corresponding curricular content and/or other information to be displayed or otherwise provided to the surgical trainee. The software may be programmed with direct visual detection algorithms including machine learning, deep learning, and/or reinforcement learning to develop the various Cue detection functions.

In another aspect, the invention provides computer software that is programmed to deliver curricular content timed appropriately to the trainee's progress on surgical training models. The software is based on an algorithm decision tree that selects appropriate content for any given surgical training session or scenario. The software structure allows the system to time the delivery of content to the trainee in any desired manner including immediately after a detected input, if desired. The system may be programmed to include optional playback by the trainee at any interval in the training session.

In another aspect, the invention provides computer software that summates the activities detected by the trainee and provides a performance score for individual steps taken by the trainee and/or the entire procedure of the surgical training module. The output from the Cues described above may be summated and interpreted by the machine learning based on performance differences between novices and experts, for example. The software may also be programmed to calculate a performance score or provide additional instruction to the trainee in order to improve future performance.

Additional objects, advantages and novel aspects of the present invention will be set forth in part in the description which follows, and will in part become apparent to those in the practice of the invention, when considered with the attached figures.

DESCRIPTION OF THE DRAWING FIGURES

The above-mentioned and other features and advantages of this invention, and the manner of attaining them, will become apparent and be better understood by reference to the following description of the invention in conjunction with the accompanying drawing, wherein.

DETAILED DESCRIPTION OF A PREFERRED EMBODIMENT

The surgical training system in its most basic form includes a surgical model, a computer (having the usual computer components including for example, but not necessarily limited to, a processor, memory, input-output interface, graphic user interface (GUI), etc.), one or more "Cue Receivers" for receiving data inputs in the form of Model Cues and/or ID-Motion Cues and/or Still Picture/Video Cues, and surgical training system software ("STSS") running on the computer processor. The surgical model may be any organ and/or other anatomical component found in any animal or human type. The Cue Receiver may include any one or combination of AR headset, microphone, digital camera, digital video, electronic sensors, real-time clock, touchscreen, computer keyboard, joystick, mouse, trackball, image scanner, graphics tablet, overlay keyboard, for example. More than one type of Cue Receiver may be provided on the same device (e.g., AR headset). The Cue Receiver relays the received Cue to the STSS which is programmed with one more surgical training sessions or modules. The STSS is programmed to receive and respond to received Cues generating appropriate output and teaching a surgical trainee to perform a surgical procedure on the surgical model.

Figure 1A:
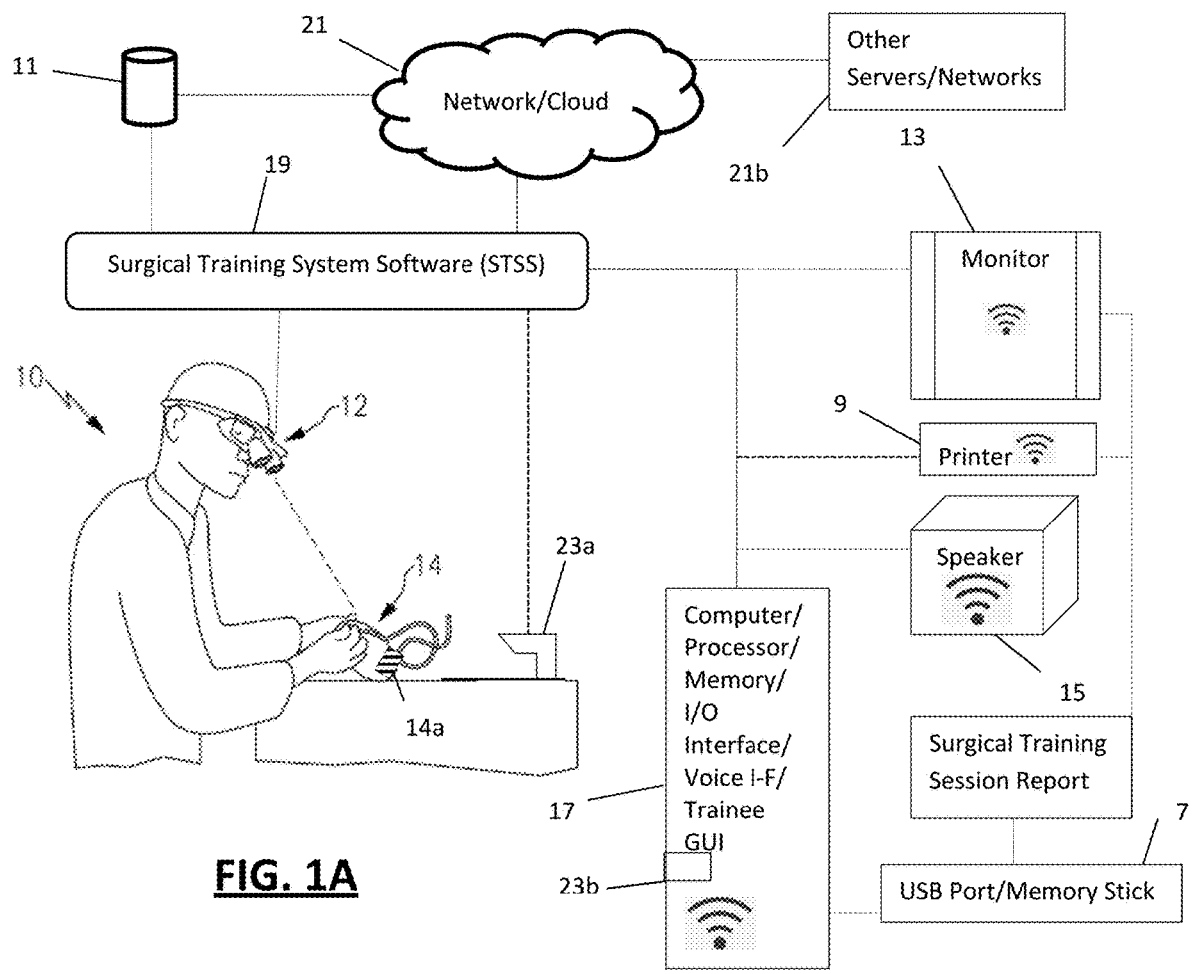
FIG. 1A is a perspective view of an embodiment of the invention showing an example of a surgical trainee utilizing an embodiment of the surgical training system.

Referring to FIG. 1, a surgical trainee 10 is seen wearing an augmented reality (AR) headset 12 and is operating (i.e., is performing a surgical training session) on a surgical model 14 which may be of any desired material (e.g., silicone, hydrogel, etc.). The AR headset 12 may include any one or more but preferably all of the following features or their equivalents:

1080p DLP Projected Display Waveguide with See through Optics
WiFi & Bluetooth Connectivity
8 Megapixel Camera
Quad Core ARM CPU
Right Eye Monocular
Haptic Feedback
Voice Control
Android 5 OS
Noise Cancelling Microphone
On Board Video Recording Media The AR headset 12 may be wired or wirelessly connected to a computer having a graphic user interface ("GUI") 17 which may be in the form of a smart phone running the STSS 19 as a downloaded software application ("app"), for example. The STSS may also be hosted remotely in the "cloud" 21 and provided to a trainee as Software as a Service (SaaS). Any other computer types may be used such as tablets, laptops, desk tops, virtual desk top, etc., whereon the STSS may be installed or accessed as a SaaS. The STSS 19 may be programmed to present to the trainee a login screen on device 17, monitor 13 and/or AR headset 12 wherein the trainee may have a password protected data file which will store the trainee's surgical training session data for later retrieval and/or playback. The STSS may connect to other servers and/or networks such as at 21b whereby the trainee's STSS file may be connected to the trainee's personal student data files hosted on, for example, the trainee's medical school server. As such, the trainee's time spent on simulated surgical training may be logged for the trainee's class credit or other purposes.

The STSS 19 may be programmed to include one or more of different surgical training sessions for selection by the trainee which may be made by voice command or via the GUI on device 17, for example. The surgical training model 14 may include a bar code 14a or the like which may be scanned by a separate bar code scanner 23a connected to the computer 17 through a wired or wireless connection or a scanner 23b integral to the computer 17 (e.g., a scanner app of a smart phone 17) or the STSS app running thereon which is operable to read the bar code on the model 14 and thereby identify the surgical model anatomy type the trainee wishes to train on. Each surgical model type programmed into the STSS may be associated with and displays to the trainee one or more surgical training sessions which are appropriate to the model type. For example, the model type may be identified as a kidney and the matching surgical training session options may be presented in a list to the trainee (e.g., on media interface 17, monitor 13 and/or AR headset 12) as, e.g., (1) tumor resection; (2) kidney stone removal; (3) vessel rupture repair, etc. The trainee may select (input) the desired surgical training session (e.g., by manual input using a graphic user interface (GUI) and touchscreen, keyboard, or mouse, and/or by visual (e.g., eye tracking) and/or voice command) and the STSS is programmed to respond to the input by launching the trainee's chosen surgical training session of the STSS program. Depending on the training session chosen, certain sensor features of the model may be automatically activated by the STSS (but not necessarily triggered) as discussed further below.

As mentioned above, the computer input by a Cue Receiver such as the AR headset 12 during a surgical training session may include Cues in the form of any one or combination of Model Cues and/or ID-Motion Cues and/or Still Picture/Video Cues. The various Cue inputs are analyzed by the STSS as they are received via the Cue Receiver with the STSS responding by generating output in the form of corresponding curricular content and/or other useful information (e.g., alerts of a surgical emergency being detected, an unsafe procedure being performed, amended or supplanted protocol to follow due to a deviation from protocol, etc.). The STSS output may be provided in any one or a combination of desired formats including audio output and/or display on the AR headset 12 and/or on a separate video monitor 13 and/or speaker 15 in the operating training room. The generated audio output may be provided to the trainee in the form of alarms and/or verbal instructions, for example. As such, in this embodiment the trainee receives the generated output for their consideration during the training (real time) so that they may understand whether their performance is correct, in general need of improvement and/or require they implement a change to the surgical protocol itself to rectify or address any identified issues with their performance. The form and content of the generated output may be programmed into the STSS for each specific surgical training session. The content may be in the form of educational curriculum stored in a database 11.

Figure 1B:
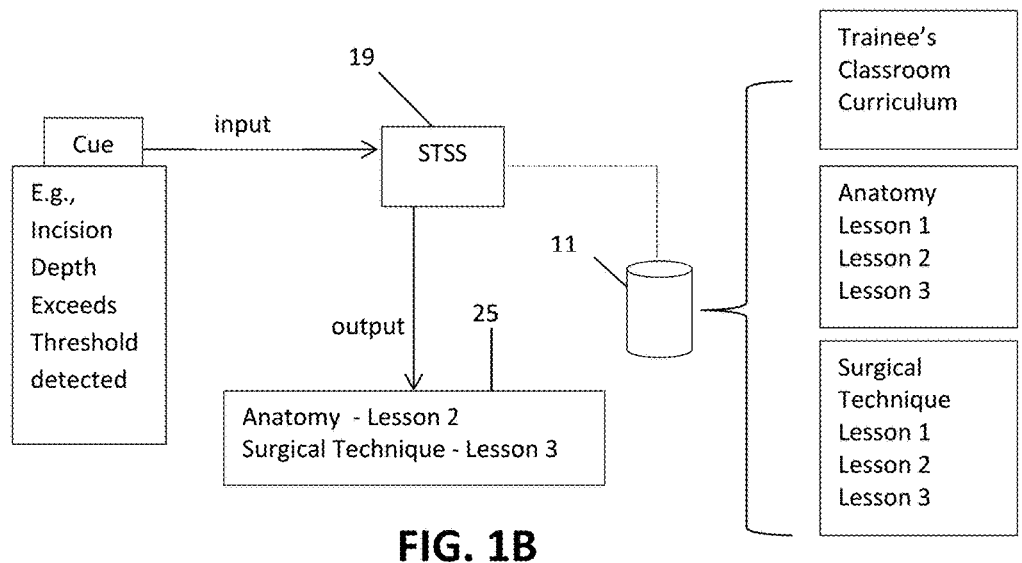
FIG. 1B is flow chart diagram of an embodiment showing a Cue input, STSS, STSS database and output.

Referring to FIG. 1B, an example of input to STSS and generated output is seen where the trainee's classroom curriculum content is stored in database 11 and is accessible by the STSS 19. In this example, a Cue has been generated and received by the STSS that the trainee made an incision which exceeded the threshold incision depth for the surgical session. The STSS is programmed to generate as an output specific curriculum content from the database 11. In this example, exceeding the incision depth threshold is an act that is tied to Anatomy Lesson 2 and Surgical Technique Lesson 3. These are thus provided as output as seen in box 25 and the trainee can then read these lessons either during or after the session to improve incision making performance.

Figure 1C:
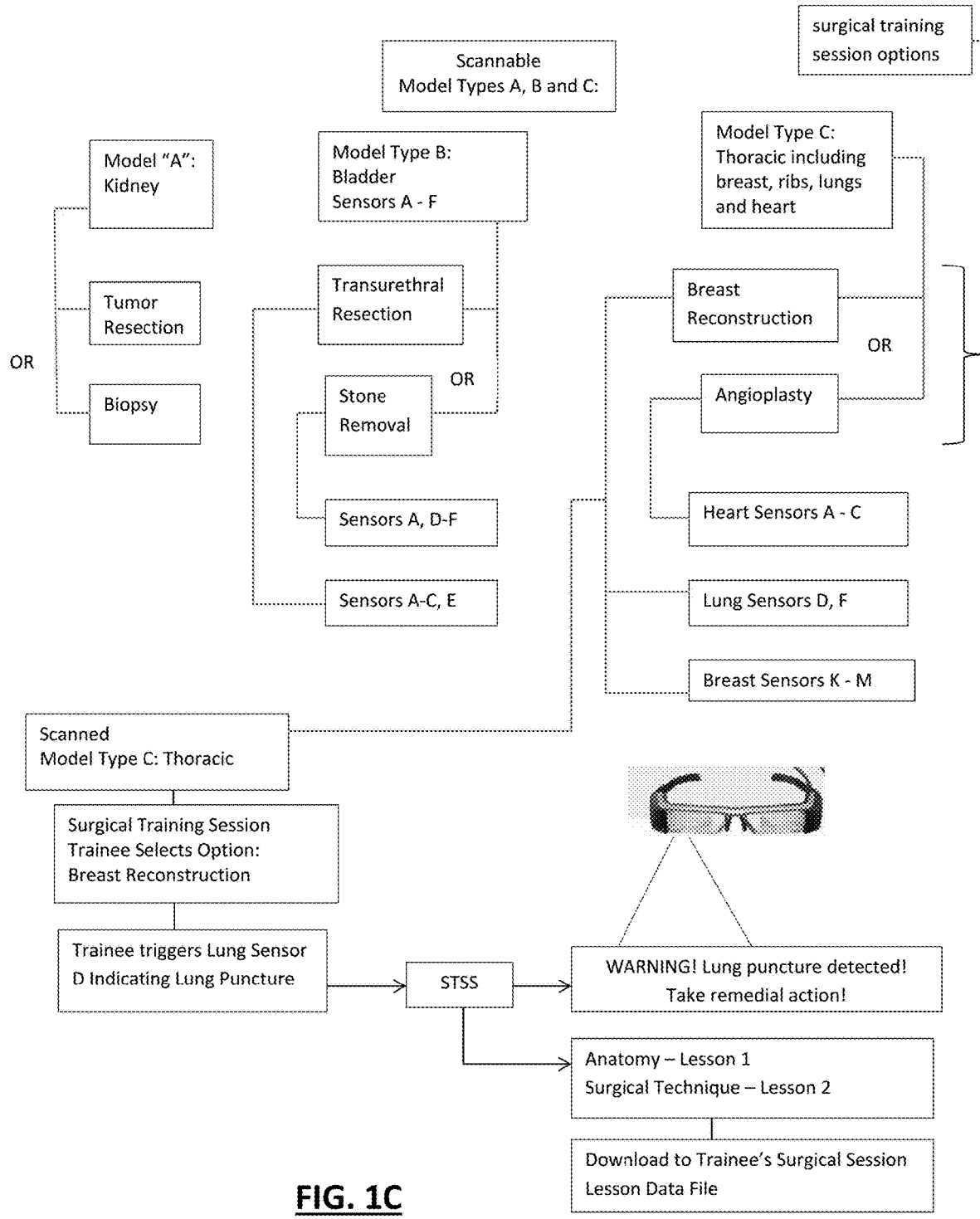
FIG. 1C is a flow chart diagram of an embodiment showing model type and training options for each model type including an example of adjacent organ sensor activation output.

FIG. 1C illustrates a box diagram showing the scanned identification of the model type where the STSS program may provide multiple surgical session choices for each of the model types. The surgical training system may comprise two or more models with each model being a distinct anatomical model type. The software training program may thus include a separate surgical session program correlated to each model type. The separate surgical session program may further include at least two alternate surgical session types. A trainee selects (e.g., via interface 17) a surgical session and certain ones of the sensors for that model and surgical session are identified as those that will be utilized during that particular training session. For example, if the trainee scans a model of a kidney, the STSS presents the list of available surgical sessions for the kidney model which in this example are "Tumor Resection" or "Biopsy". The trainee selects the model training session (e.g., via interface 17) which causes STSS to launch the program for the chosen session. As mentioned above, the surgical models and sessions may have a unique set of sensors that are utilized for the particular surgical model and session chosen. In the bladder model example, the trainee may select either the Transurethral Resection or the Stone Removal training sessions. Selection of the Transurethral Resection may activate sensors A and D-F (e.g., power them to a "ready" state via the sensor's firmware, if present) as these sensors are the ones that are associated with performing that particular surgical session. Should the trainee instead select the stone removal session, the set of sensors associated with that particular surgical session are activated which in this example are sensors A-C and E. For example, if the chosen model is the Thoracic model including models of the breast, ribs, lungs and heart, the trainee is presented with the surgical session choices of Breast Reconstruction and Angioplasty. If the trainee selects Breast Reconstruction, the set of sensors associated with that procedure are activated which include lung sensors D and F and breast sensors K-M. Sensors in adjacent models may be important to indicate if the trainee is wrongly invading the space of the adjacent model structure (e.g., puncturing a lung while working on the breast). Thus, as seen in box 31 of FIG. 1C, the surgical trainee has scanned the Thoracic (model type C) into the STSS which provides the trainee with the choice of performing a breast reconstruction or an angioplasty. The surgical trainee selects the breast reconstruction training session at box 33 which launches that particular training session program of the STSS. During the surgical training session, should the trainee mistakenly cut into and puncture the lung, lung sensor D sends a signal to the STSS via a Cue Receiver and the STSS is programmed to respond by providing the trainee with an output which may be in the form of a visual warning message in the AR headset of the lung puncture and need to take remedial action. The STSS may also provide as an output the curriculum content from database 11 corresponding to a lung puncture. The output may be provided in any desired format and on any media (e.g., on monitor 13, printed on printer 9, and/or digitally stored in the memory of computer 17 or on a separate memory storage device such as memory stick 7 for later retrieval by the trainee, etc.).

Figure 2A:
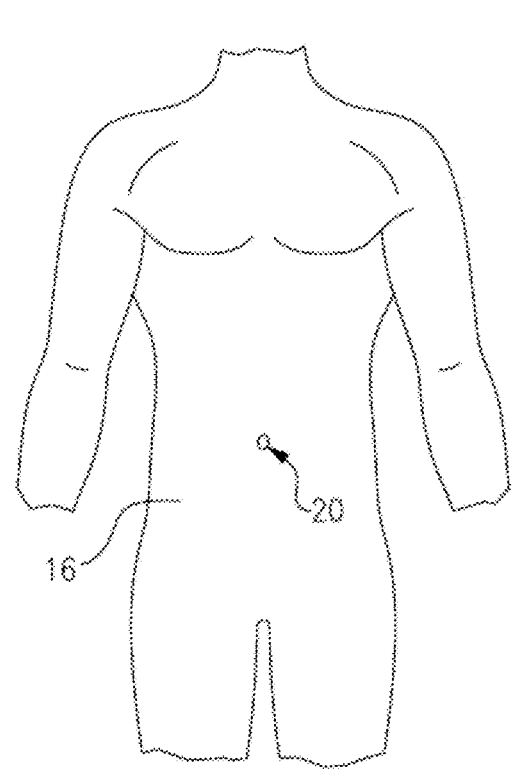
FIG. 2A is a fragmented plan view of an example of surgical phantom model.
Figure 2B:
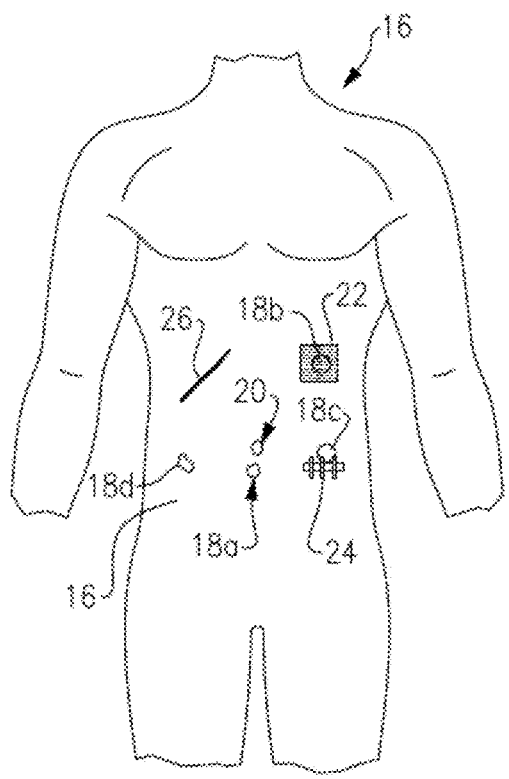
FIG. 2B is the view of FIG. 2A showing markings on the model in accordance with an embodiment of the invention.

An example of a surgical training session is seen in FIGS. 2A and 2B wherein a surgical phantom model of a human abdomen 16 is seen at the start of the laparoscopic or robotic surgical training session. Port locations are designated by reference numerals 18a-18d and represent the locations where openings in the abdominal wall (ports) are to be formed by the trainee during the training session. The torso navel or umbilicus is indicated by reference numeral 20 and provides a reference point (fiducial) for establishing the general orientation of the model in 3D space. In this surgical training session example, the trainee is directed by the STSS via audio and/or visual display in AR headset 12 and/or by a separate instruction (which may be in verbal or written form, for example) to place a first umbilical port 18a adjacent navel 20. The trainee 10 may further be directed to the proper placement of umbilical port 18a by the STSS which may be programmed to cause the AR headset 12 to superimpose an image of where port 18a should be placed onto the surgical model 16. Placement of port 18a causes a Cue (either by detecting changes to model appearance, trainee motion, or surface or embedded sensors, for example) to be detected which triggers generation of an input (e.g., electronic signal) to a Cue Receiver such as AR headset 12. The AR headset 12 (Cue Receiver) relays the signal to the STSS which is programmed to analyze the input and determine if the input indicates that the trainee performed proper placement of port 18a. If so, as explained further below, the trainee may then be guided by the STSS to place the second port 18b in a location designated by bar code 22. Although a bar code 22 is shown in FIG. 2B for the ease of description, it is understood that any type of Model Cue which can be sensed by a Cue Receiver (e.g., AR headset 12) may be used which may or may not be visible to the human eye. Such indicators include, for example, invisible inks which are detectable by the AR headset 12 but not the trainee even while wearing the AR headset 12. This may be desirable as it would require the trainee to find the proper port location on the torso without it being immediately recognizable by visual or other indicators. In this case, the trainee may be simply instructed by the STSS to place the second port without being shown where that second port is supposed to be placed. The non-visible Model Cue at port location 18b or other Cue such as the Still Picture/Video Cue may be used to detect if the trainee placed the port in the correct location or not.

As stated above, if it is desired to show the trainee the proper port location, the STSS may cause either an image of an abdomen with the port in the trainee's AR headset, or overlay an image of the port location onto the surgical model. The AR headset recognizes the correct location of the port location 18b by any desired Cue such as a surface marking such as by scanning barcode 22 or other fiducial such as navel 20. Again, this may be as subtle as a slight color change in the model or use of applied inks or other colorants outside the human visible spectrum to prevent trainees from relying too heavily on such markings which may not be present in actual surgery.

After second port 18b is correctly placed as detected by the appropriate Cues which relay their received data as input to the STSS (see discussion above), the trainee is directed by the STSS via AR headset 12 to place a third port 18c at location 24 which may include a Cue in any desired form including, for example, the form of a bar code on the model as described above or a sensor which may or may not be embedded in the model (and thus not visible to the human eye) that is detectable by the AR headset 12. The sensor (e.g., a pressure sensor) may, upon activation, generate a signal which is detected by the AR headset 12 which informs the STSS that third port 18c has been properly placed which is programmed to respond by generating guidance to the trainee (e.g., by issuing text and/or verbal instructions in AR headset 12 and/or monitor 13 and/or speaker 15) to place fourth port at 18*d*. After a laparoscopic training procedure is finished as detected by a Cue and relayed to the STSS, the trainee may be instructed by the STSS to remove a specimen from the model (e.g., simulated tumor) and instruct the trainee to create an incision at 26.

Figure 3A:
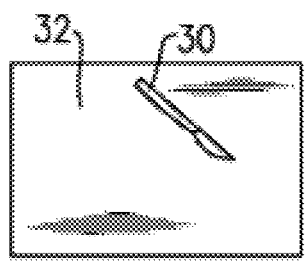
FIG. 3A is a fragmented plan view of the model seen in FIG. 2B and further showing a surgical instrument for use by the surgical trainee on the model in accordance with an embodiment of the invention.
Figure 3B:
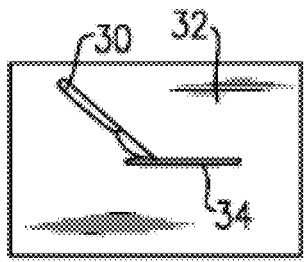
FIG. 3B is the view of FIG. 3A showing the surgical instrument in the process of making an incision in accordance with an embodiment of the invention.
Figure 3C:
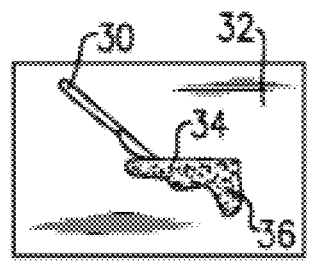
FIG. 3C is the view of FIG. 3B showing simulated bodily fluid (eg; blood, bile, urine, etc.) exiting the incision in accordance with an embodiment of the invention.

Referring now to FIGS. 3A-C, another aspect of the invention may include the use of image recognition of the trainee's progress to guide the surgical training session through the STSS. In FIG. 3A, a surgical instrument in the form of a scalpel 30 is shown above a surgical model surface 32 (trainee's hand not shown in FIGS. 3A-C for the sake of clarity). The AR headset 12 and STSS may be programmed to receive (e.g., via AR headset 12) and analyze (process) relative positional data of the model surface 32, the trainee hand (not shown) and scalpel 30 and provide the trainee with information (output) as to whether the trainee is holding the scalpel 30 in the correct orientation for the task at hand (e.g., creating an incision for tumor resection).

The trainee proceeds with the surgical simulation session by cutting an incision 34 in the model surface 32 using scalpel 30. The AR headset and STSS may be programmed to calculate the length and/or depth of the incision 34 based on Cues such as visual appearance and/or fiducial references. For example, the Cue may be provided in the form of a 1 cm square fiducial detected on the model "skin" surface, and wherein the STSS may be programmed to calculate distance based on the visual detection of the incision relative to the fiducial. Alternatively, Model Cues in the form of electronic sensors could be spaced a certain distance apart and the number of sensors detected in linear or curvilinear sequence can be used for the STSS to calculate distance (length of incision).

Depth (the distance from model surface into body of the model) can be provided by a Video Cue and/or Motion Cue based on the amount of scalpel that has extended beneath the upper surface of the model or "disappeared" into the model. The scalpel blade in this case is the visual cue and is detected by the AR headset 12 which can detect and relay to the STSS what percentage of the blade has disappeared into the model. The STSS can be programmed to use this data to calculate incision depth and provide appropriate instruction to the trainee if it calculates that the incision 34 has not been correctly executed, e.g., it does not meet the minimum programmed thresholds for incision depth.

In FIG. 3C, the model surface 32 may include simulated body fluid such as simulated blood placed so that it may flow from incision 34. The STSS may be programmed to recognize this simulated bleeding 36 based on detected color differentiation (e.g., red, for blood) from model surface 32 (e.g., flesh tone), for example, and provide appropriate instruction to the trainee such as "use suction" or "hold pressure", for example.

Figure 4A:
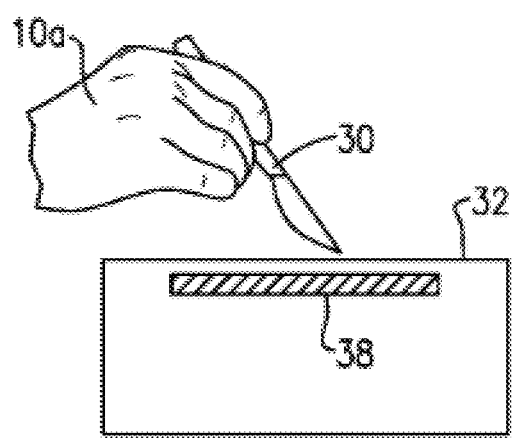
FIG. 4A is a fragmented view of a surgical training model having a Model Cue with a trainee holding a surgical instrument above the model in accordance with an embodiment of the invention.
Figure 4B:
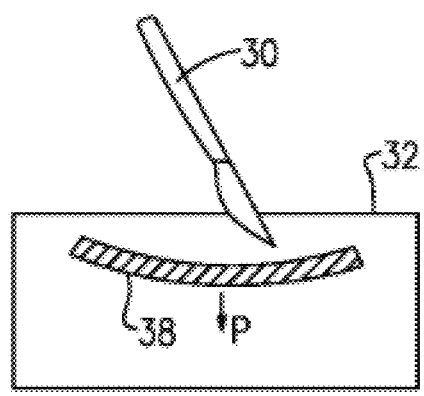
FIG. 4B is the view of FIG. 4A showing deformation and activation of the sensor applied by the surgical instrument in accordance with an embodiment of the invention.

FIGS. 4A and 4B illustrate an example of a sensor in the form of a pressure sensor 38 which is operable to detect pressures which the software programming correlates into trainee progress and performance. It is noted that while a pressure sensor is used in this example, it is understood that any type of sensor may be used including, e.g., strain sensors, flow sensors, etc. For example, the trainee's hand 10*a* is holding scalpel 30 (FIG. 4A) which cuts into model surface 32 (FIG. 4B). The sensor is seen in its resting state in FIG. 4A. The sensor 38 may be detected by the surgical instrument pressing thereagainst as seen in FIG. 4B which generates a signal causing the STSS to provide certain instructions to the trainee via the AR headset or other HCI (human computer interface). When the trainee exerts pressure on sensor 38 via scalpel 30, the sensor 38 sends a signal to a Cue Receiver which relays the signal to the STSS which causes the STSS to generate an output in the form of providing the trainee with the next set of instructions in the surgical procedure such as, for example, "place self-retaining retractor" in visual and/or audio format. The sensor 38 may also measure and transmit to a Cue receiver and the STSS the force being exerted thereon by the trainee's use of the scalpel. The STSS may compare the force values received from the sensor 38 and compare the values to preset force thresholds. If the sensed force values are outside acceptable threshold values, the STSS may respond by generating an output of this information to the trainee with the option of further instruction as to how the trainee may correct and/or improve performance.

Figure 5:
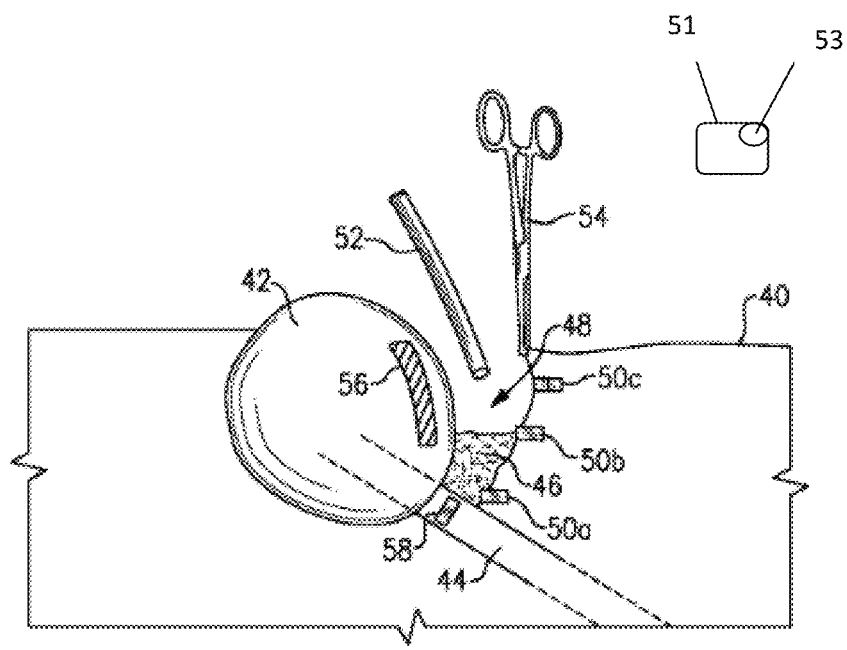
FIG. 5 is a fragmented view of a surgical model with simulated tumor in the process of being resected in accordance with an embodiment of the invention.

FIG. 5 illustrates an example of a surgical model for a surgical training session involving a tumor resection according to an embodiment of the invention. In this example, various sensors are employed to drive the trainee curriculum content based on sensed trainee performance metrics. The trainee (not shown) surgical training session on surgical phantom model 40 directs the trainee to resect tumor 42 with a feeding blood vessel 44. As the trainee resects tumor 42, the blood vessel 44 is cut releasing simulated blood 46. The simulated blood 46 begins to fill the resection cavity 48 which is sensed by sensors 50*a* and 50*b*. It is noted that the sensors may be strategically positioned as shown such that they can sequentially detect the amount of blood filling cavity 48. For example, triggering of sensor 50*a* but not sensors 50*b* or 50*c* may indicate the presence of "n" cubic centimeters ("cc's") of blood in cavity 48. As more blood enters cavity 48, sensor 50*b* is triggered which indicates the presence of "n+1" cc's of blood. As even more blood enters cavity 48 sensor 50*c* is triggered indicating "n+2" cc's of blood in cavity 48. Any number of sensors may be strategically placed in the model to detect an increase in the amount of blood. Depending on the type and sensing range of the sensors employed, the sensors may be chosen so as to be activated only upon physical contact with the simulated blood or they may be activated whenever the simulated blood is within a predetermined distance of the sensor warning the trainee that the bleeding may be worsening.

The STSS programming may be made such that it selects information to provide the trainee based on which and/or how many and/or the order of sensors which are activated during a specific training session or any segment thereof. In the example shown in FIG. 5, simulated blood 46 has reached the level of sensor 50*b* which may prompt the STSS to provide instructions to the trainee to better utilize the suction tube 52. If the simulated blood 46 reached the level of sensor 50*c*, the STSS programming may provide instruction to the trainee, e.g., by providing the trainee text (e.g., via AR headset 12) and/or voice message such as, for example: "significant blood loss is occurring—alert the anesthesiologist that there is active bleeding." A sponge 51 is also seen having a sensor 53. Should the trainee use sponge 51 and leave it inside the model upon closing the incision, the sensor 53 will signal the STSS which will alert the trainee that the sponge has been left inside the model. The STSS may also deliver curriculum content from database 11 to the trainee correlated to this mistake in procedure.

If there are multiple organs present in the model, sensors within an adjacent organ may be provided to inform the trainee if he/she has damaged or wrongly entered the surrounding space of an adjacent organ. For example, as discussed above with reference to FIG. 1C, if the training session is on a breast model, lung models may be positioned in an anatomically correct position relative to the breast. Puncturing a lung is considered a surgical emergency. The lungs may therefore be provided with sensors that activate should the trainee knowingly or unknowingly puncture the lung. Upon such sensor activation, the STSS may issue a text and/or audible alert of the lung puncture with or without further instruction for the trainee to take corrective action. If corrective action is to be taken, such action may be analyzed (e.g., by video and/or other Cues) and timed to determine if the trainee acted in accordance with STSS programmed accepted surgical corrective action protocols.

The STSS programming may instruct the trainee to continue the training session at any time during the session. For example, the programming may provide the trainee instructions to use suction tube 52 and forceps 54 to retract tumor 42. As the trainee retracts the tumor with the use of suction tube 52 and/or forceps 54, a pressure sensor 56 embedded in tumor 42 may be pressed upon and thus activated. The STSS programming may include threshold pressure values indicative of correct retraction pressure. If insufficient retraction occurs based on low signal from tumor pressure sensor 56, the STSS may provide an alert to the trainee, e.g., to use suction tube 52 to perform more retraction.

This tumor resection training session may be programmed in the STSS to require ligation of blood vessel 44 as part of the procedure for tumor removal. The STSS programming will recognize ligation of vessel when sensor 58 senses a threshold pressure. If a suture is placed around vessel 44 but is not sufficiently tight, the STSS programming can instruct the trainee to redo or tighten the suture to prevent further bleeding, for example.

Figures 6A, 6B:
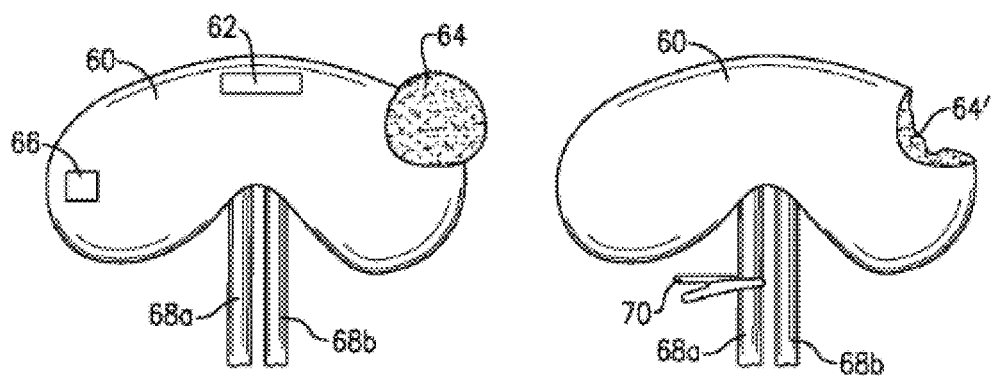
FIG. 6A is a fragmented plan view of a surgical model of a human kidney having a simulated tumor in accordance with an embodiment of the invention.
FIG. 6B is the view of FIG. 6A showing the simulated tumor resected and a temporary clip positioned on the renal artery in accordance with an embodiment of the invention.

FIGS. 6A and 6B illustrate examples of Model Cues provided in surgical phantom model 60 intended for kidney tumor resection training. Kidney tumor model 60 is identified by the STSS programming by scanning barcode 62 (e.g., with a barcode reader forming a part of AR headset 12 or with a separate barcode scanner such as 23a or 23b seen in FIG. 1. Barcode 62 may cause the STSS programming to provide the trainee curricular content matched to the specific surgical training session (in this example, kidney tumor resection). Note barcode 62 is one of many possible examples of model type marking as a Model Cue. As discussed above, other examples of sensor detectible markings include subtle color differentiation between the marking and the model substrate and/or inks or other colorants outside the human visible spectrum so as to prevent the trainee from noticing the markings which might otherwise create an unrealistic training experience as such markings will not appear in an actual surgical procedure.

Simulated kidney tumor 64 and its border may be identified by the STSS programming by sensed color difference between the tumor 64 and the kidney model substrate 60 surrounding the tumor 64. The edge of the kidney model 60 (which in a real kidney is typically covered by fat) has unique markings that are detected and inform the STSS programming that this portion of the kidney has been exposed. The trainee is required to evaluate the entire kidney during surgery to ensure that there are no missed lesions or other abnormalities. The STSS will instruct the trainee to "uncover" or "expose" the kidney until marking 66 is detected by the STSS programming.

During resection of the tumor 64, the trainee must identify the renal artery 68a and renal vein 68b. The STSS programming provides instruction to the trainee to place a temporary clip 70 on only artery 68a. If incorrectly placed (as detected by any one or more of Model Cues and/or ID-Motion Cues and/or Still Image/Video Cues), the STSS programming may provide instructions to the trainee that the clip has been improperly placed and/or instruct the trainee to move clip 70 to the correct position. For example, should the trainee place the clip on the vein 68b, this would be detected (e.g., by a sensor placed in or on vein 68b or by visual input through a camera) and the STSS programming would identify it as a medical emergency as placement on the vein would cause the kidney to have blood flow in but not out potentially causing the kidney to burst. Furthermore, the correct clip position is perpendicular to the vessel and the tips of the clip should cross the edge of the vessel. Visual inspection (e.g., color difference between clip and vessel) may allow the STSS to assess any overlap and relative positioning of the clip relative to the artery.

Referring to FIG. 6B, residual tumor is indicated by reference numeral 64'. The STSS programming may recognize residual tumor 64' based on visual data (e.g., Still Image/Video Cues) such as remaining color differentiation from the surrounding area. The STSS programming may then instruct the trainee to continue with the tumor resection until all residual tumor 64' is removed. After residual tumor 64' is completely removed as recognized by a received Cue (e.g., no remaining color differentiation seen in the visual data), the STSS programming may then instruct the trainee to continue with the training session and remove temporary clip 70 to restore blood flow to the kidney.

Figure 7:
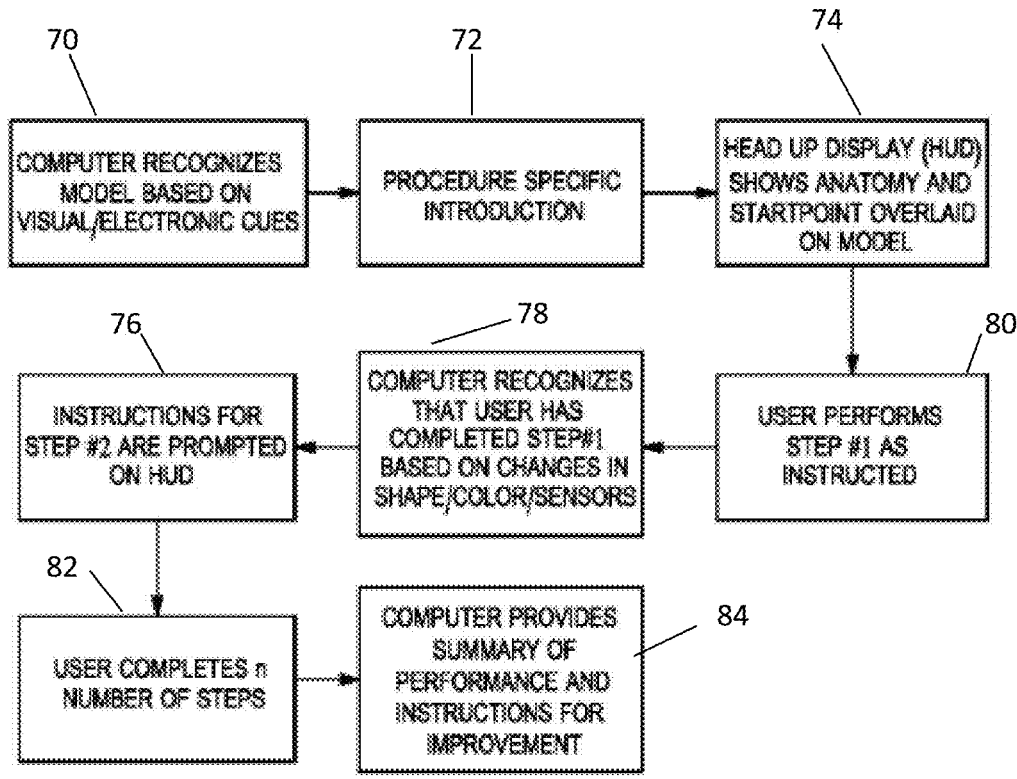
FIG. 7 is a flow diagram of a surgical training process in accordance with an embodiment of the invention.

FIG. 7 illustrates a process for training of the STSS using readily available machine learning software. STSS training is an offline process performed by taking the Cues of interest in identifying (e.g., suture quality) by using machine learning software for image process training.

Figure 8:
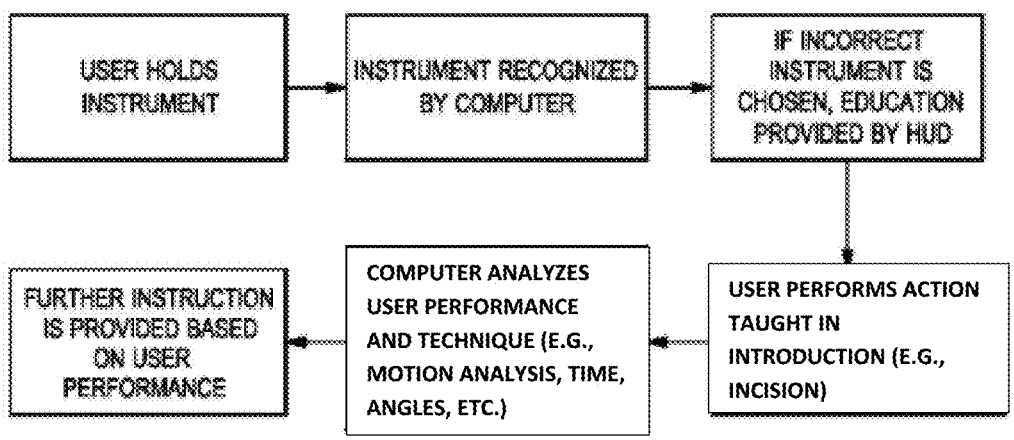
FIG. 8 is a flow diagram of a surgical training process in accordance with an embodiment of the invention.

In FIG. 8, preprocessed image characteristic data generated as seen in FIG. 7 is used in real time by multiple (typically hundreds) of GPUs (generalized processing units) and/or multiple application specific digital logic elements within a Field Programmable Gate Array(s) (FPGA(s)), and/or Application Specific Integrated Circuit (ASIC) to provide a probabilistic estimate of the likelihood that image is a particular object or image characteristic. This real time image processing approach allows surgical progress to be identified using Cues, interpreted by the STSS, and provide appropriate instruction to provide training during simulation activity. In this example, the cue is a user's hand and instrument are the cues. Both type of object and technique using object are analyzed and then corrected by the computer if deemed necessary.

Figure 9:
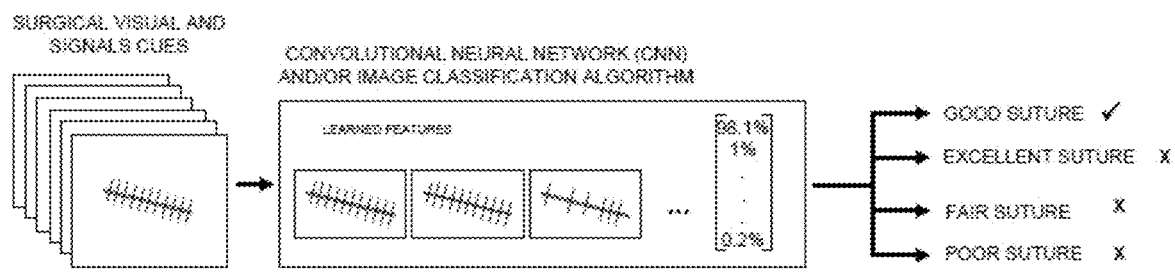
FIG. 9 is a flow diagram of training a computer for machine and deep learning using neural networks according to an embodiment of the invention.

FIG. 9 is a flow diagram of training a computer for machine and deep learning using neural networks according to an embodiment of the invention. Incision spacing is used as an example for detection of user technique. The first box represents the input to the cue receiver (a stack of images from the AR headset video). A neural network classifies suture pattern based on a learned image database and determines the spacing distance between sutures. The spacing is compared against novice/expert use data and the output is a performance score such as percentile. The set threshold for acceptable suture spacing and error then prompts the STSS to inform user of suture quality and acceptability.

Figure 10:
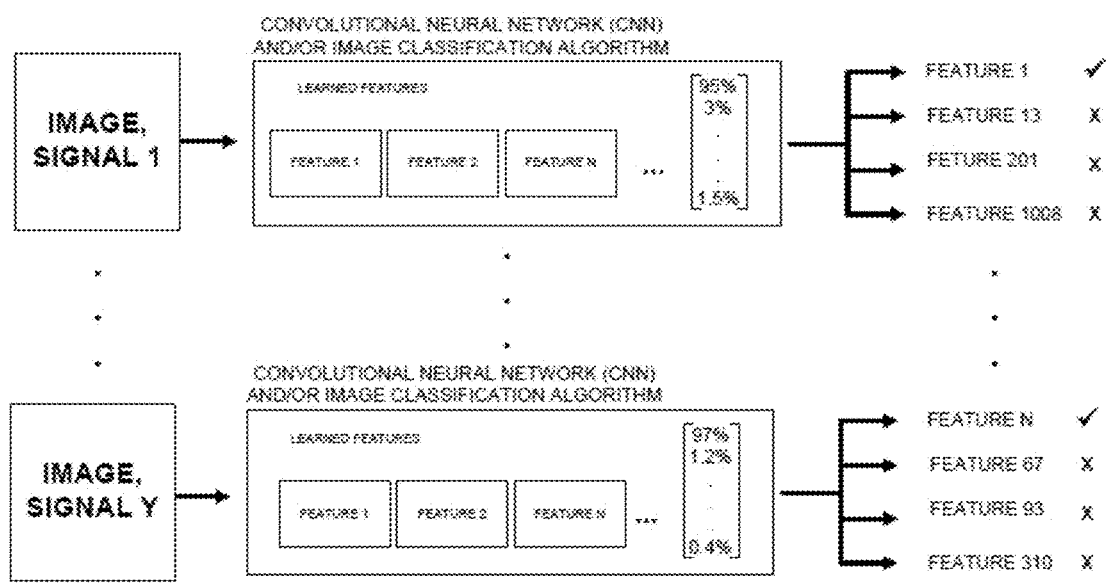
FIG. 10 is a flow diagram of real time object/signals detection using machine/deep learning according to an embodiment of the invention.
Figure 11:
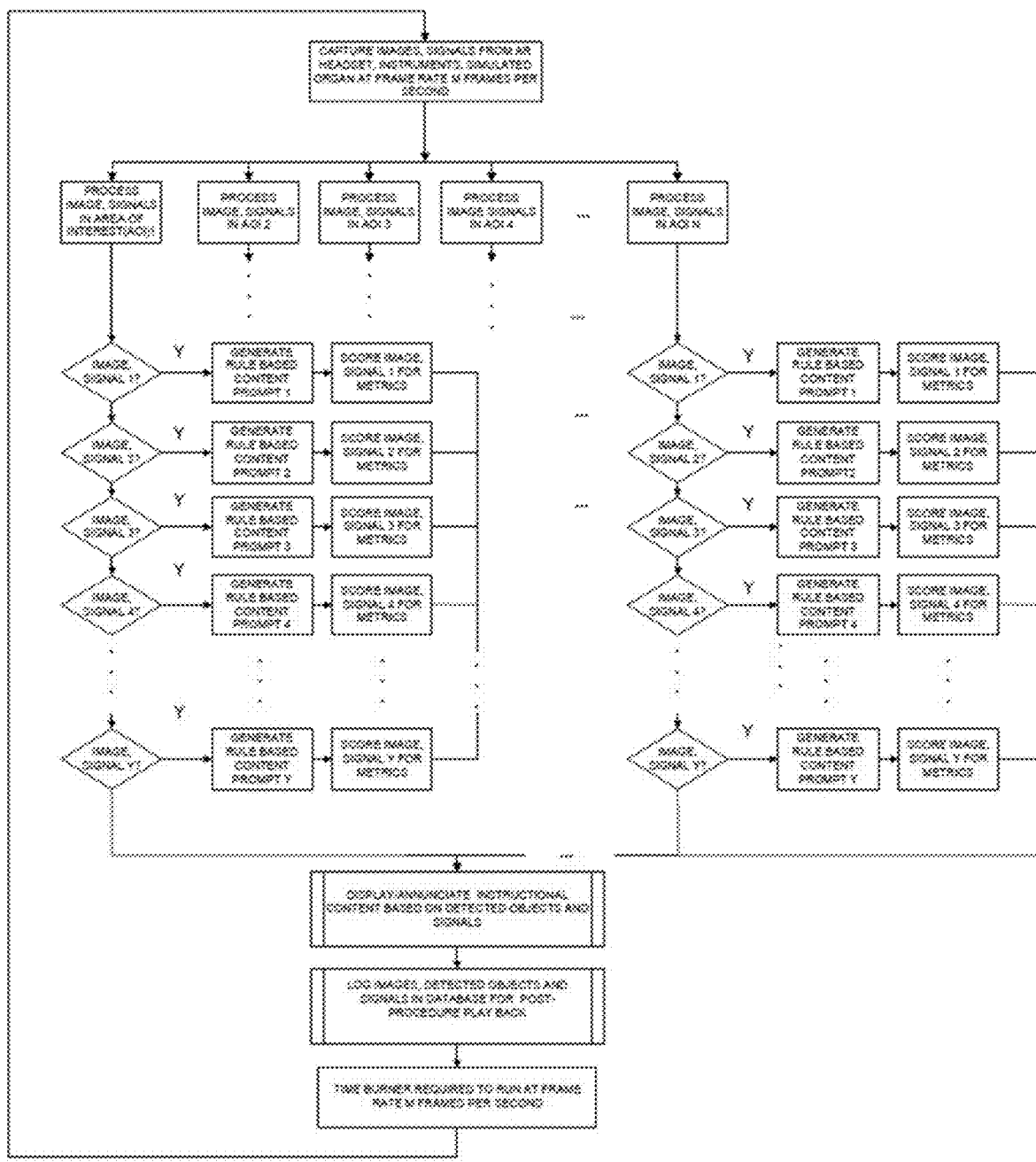
FIG. 11 is a flow diagram of a signal decision tree and curriculum content delivery according to an embodiment of the invention.

FIG. 10 is a flow diagram of real time object/signals detection using machine/deep learning according to an embodiment of the invention;

FIG. 11 illustrates a decision tree depicting "N" instances of the process of FIG. 9 running in parallel on multiple GPUs, ASICs and/or FPGAs to identify "Y" objects/signals in the area of interest (AOI) which can be used by the STSS to generate various system output and prompts. Additionally, images can be classified and scored to be used for metrics and for figures of merit. For example, attributes such as suture spacing, wound gap or other surgical attributes known to be desirable for improved surgical outcomes. Figures of merit could be excellent, good, fair and poor, for example. This processing is performed iteratively at frame rate "M", which is normally run at 30-100 Hz for simulated images and/or signals. During each frame, object detection is performed utilizing machine learning, followed by a process which displays/annunciated instructional content based on objects detected. Next, classified objects and signals are time stamped and stored in a database for post procedure instructional playback. Lastly, a "time burner" task will run which accounts for unused processing time, and synchronizes the processing at rate of M frames per second.

Figure 12:
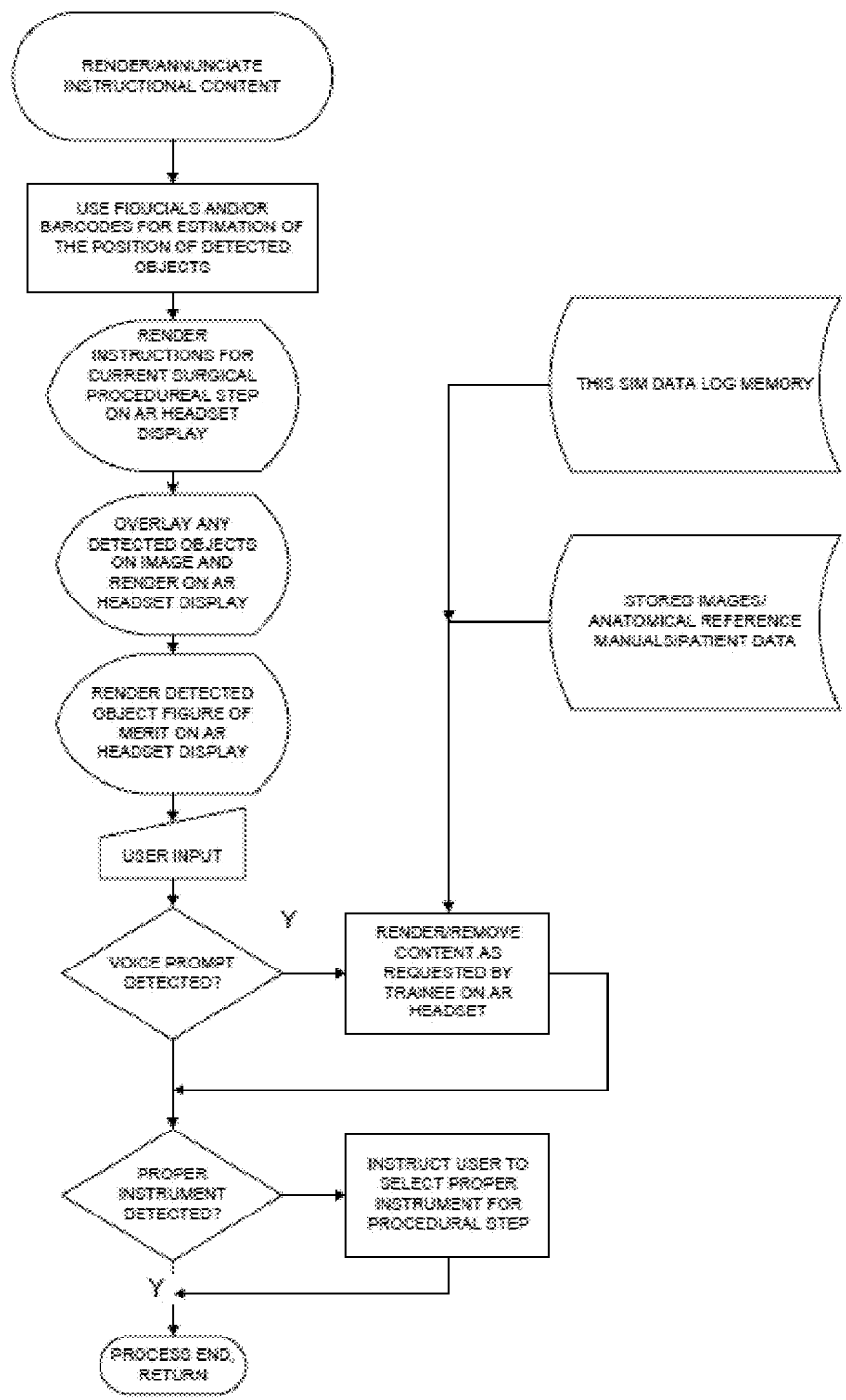
FIG. 12 is a flow diagram of instructional content based on detected objects and signals according to an embodiment of the invention.

FIG. 12 illustrates how instructions may be rendered on the AR headset 12 to prompt the trainee for the next step in the surgical procedure. Fiducials and/or barcodes are used to estimate the position of detected objects within the surgical field of view. Objects detected during the signal/object detection phase can be overlaid on an image of the area of interest and displayed on the AR headset 12 for viewing by the trainee 10. For instance, if a surgical trainee is learning suturing, an overlay can be rendered showing their instantaneous score or figure of merit of their suturing technique. For instance, the trainee can provide voice prompt input, such as "advance instructions to the next step" though the HCI. Additionally, machine learning can also detect whether or not the trainee is using the correct instrument for a particular phase of the training session, and prompt the trainee with the correct instrument.

Figure 13:
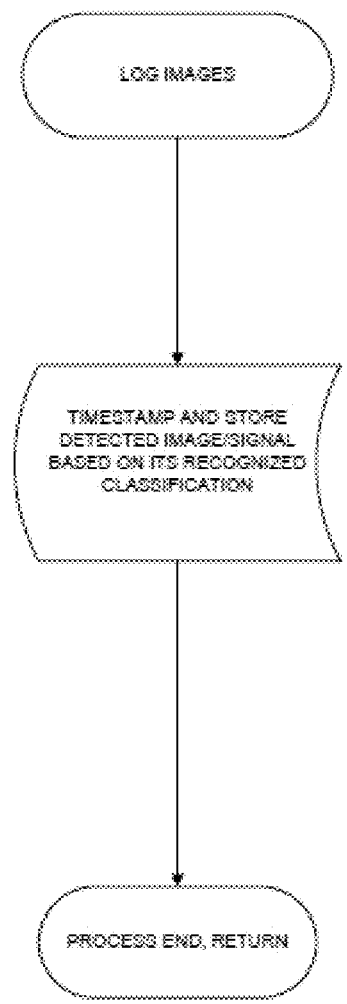
FIG. 13 is a flow diagram of image timestamp and log according to an embodiment of the invention.

FIG. 13 illustrates Log image/signal putting a timestamp on detected objects and storing them in a database for later retrieval during playback/debrief mode.

Figure 14:
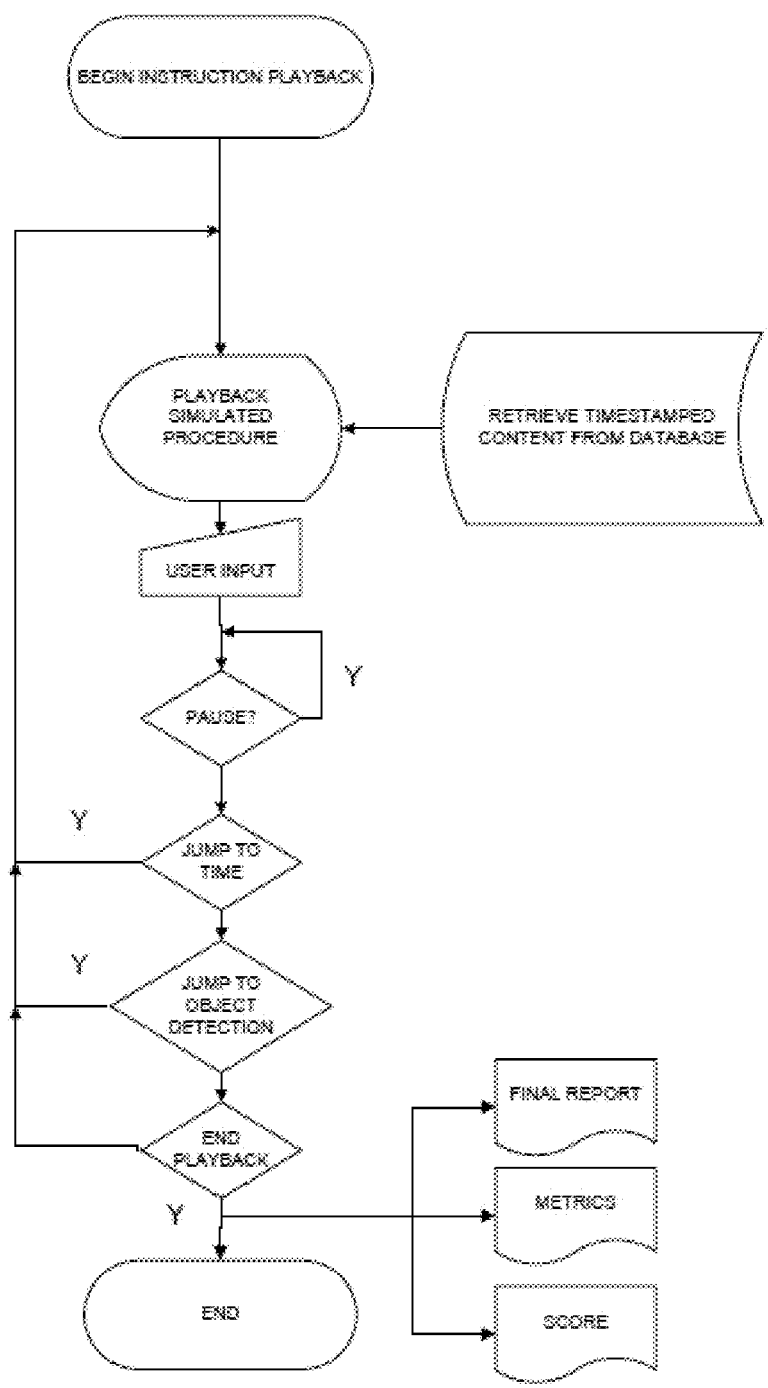
FIG. 14 is a flow diagram of curriculum instruction playback mode according to an embodiment of the invention.

FIG. 14 illustrates instruction playback mode which retrieves the training session using physical simulated organs and time synchronized AR video/audio/signals from the time-stamped database. Playback can be started at any part of the training session in an interactive manner with the trainee. For instance, the user can pause the playback at will, jump to a specific time during the training session, jump to the next instance of a detected object, or end the playback session. Reports will be generated at the end of the record/playback session and can include metrics, scores and a final report record.

While the apparatus, methods and systems of the invention have been shown and described with reference to certain preferred embodiments thereof, it will be understood by those skilled in the art that various changes in form and details may be made therein without departing from the spirit and scope of the invention as described.

What is claimed is:

1. A surgical training system, comprising:
   a) a model of an anatomical part of a human or animal, said model having one or more cues;
   b) a cue receiver operable to receive one or more cues from said model, said cue receiver being operable to generate a signal in response to receiving a cue;
   c) a computer processor operable to receive signals from said cue receiver;
   e) a computer database having surgical training curriculum having one or more individual surgical subject matter components stored therein; and
   f) a software program running on said computer processor and connected to said database, said software program operable to correlate said one or more received signals to said one or more individual surgical subject matter components, said software program being further operable to provide as an output the individual surgical subject matter component which is correlated to a received signal;
   wherein said cue receiver is an augmented reality headset.

2. The surgical training system of claim 1, wherein said augmented reality headset having one or more of the following:
   a) projected display waveguide with see through optics;
   b) WiFi and Bluetooth connectivity;
   c) camera;
   d) central processing unit;
   e) monocular;
   f) binocular;
   g) haptic feedback;
   h) voice control;
   i) operating system;
   j) noise cancelling microphone; and
   k) on board video recording media.

3. The surgical training system of claim 1 wherein said cue receiver includes a digital still and/or video camera.

4. The surgical training system of claim 1 wherein said cue is a barcode attached to said model and said cue receiver includes a bar code scanner.

5. The surgical training system of claim 1 wherein said software program is provided as software as a service.

6. The surgical training system of claim 1 wherein said output is provided on a computer monitor.

7. The surgical training system of claim 1 wherein said output is provided on said augmented reality headset.

8. The surgical training system of claim 1 and further comprising two or more of said models with each model being a distinct anatomical model type, and wherein said software program includes a separate surgical session program correlated to each of said model types.

9. The surgical training system of claim 8 wherein said separate surgical session program includes at least two alternate surgical session types.

10. The surgical training system of claim 9 wherein said anatomical part is thoracic having heart and lung models.

11. The surgical training system of claim 9 wherein said model type is kidney and said surgical session types include a tumor resection surgical session and a biopsy session.

12. The surgical training system of claim 1 wherein said anatomical part includes at least two models and wherein said software program is programmed to provide an output in response to signals received from either of said models.

* * * * *